(12) United States Patent
Rocher et al.

(10) Patent No.: US 11,340,207 B2
(45) Date of Patent: May 24, 2022

(54) METHOD AND INSTALLATION FOR DETERMINING AN IMPROVED MINERALOGICAL COMPOSITION OF A ROCK SAMPLE

(71) Applicant: Geoservices Equipements, Roissy en France (FR)

(72) Inventors: Yohann Rocher, Roissy-en-France (FR); Mahdi Ammar, Roissy-en-France (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 886 days.

(21) Appl. No.: 16/103,254

(22) Filed: Aug. 14, 2018

(65) Prior Publication Data
US 2019/0056374 A1 Feb. 21, 2019

(30) Foreign Application Priority Data
Aug. 16, 2017 (EP) .................... 17290103

(51) Int. Cl.
*G01N 33/24* (2006.01)
*G01N 23/223* (2006.01)
(Continued)

(52) U.S. Cl.
CPC .......... *G01N 33/24* (2013.01); *G01N 23/207* (2013.01); *G01N 23/223* (2013.01);
(Continued)

(58) Field of Classification Search
CPC .. G01N 33/24; G01N 23/2206; G01N 23/223; G01N 23/207; G01N 2223/306;
(Continued)

(56) References Cited

U.S. PATENT DOCUMENTS

| 9,310,514 | B2 * | 4/2016 | Galford .................. G01V 5/101 |
| 2007/0246649 | A1 * | 10/2007 | Jacobi .................... G01V 5/101 |
| | | | 250/269.6 |

(Continued)

OTHER PUBLICATIONS

Charsky et al., "Quantitative analysis of kerogen content and mineralogy in shale cuttings by Diffuse Reflectance Infrared Fourier Transform Spectroscopy", Symposium of the Society of Core Analysts held in Aberdeen, Scotland, UK, 27-30, 2012.*

(Continued)

*Primary Examiner* — Catherine T. Rastovski
(74) *Attorney, Agent, or Firm* — Jeffrey D. Frantz

(57) ABSTRACT

A method for determining a mineralogical composition of a geological formation sample includes measuring a mineralogical composition of the sample and measuring an elemental composition of the sample. The mineralogical composition is processed to compute a predicted elemental composition of the sample based on known elemental compositions of predetermined minerals. The measured mineralogical composition is corrected to obtain a corrected mineralogical composition which is in turn processed to compute a corresponding corrected predicted elemental composition of the sample. The measured elemental composition is compared with the predicted elemental compositions to obtain error indicators. The error indicators are compared and evaluated to selected and output one of the measured or corrected measured mineralogical compositions.

20 Claims, 9 Drawing Sheets

(51) Int. Cl.
   *G01N 23/207* (2018.01)
   *G01N 23/2206* (2018.01)
(52) U.S. Cl.
   CPC ... *G01N 23/2206* (2013.01); *G01N 2223/056* (2013.01); *G01N 2223/076* (2013.01); *G01N 2223/306* (2013.01); *G01N 2223/616* (2013.01)
(58) Field of Classification Search
   CPC ....... G01N 2223/056; G01N 2223/616; G01N 2223/076
   See application file for complete search history.

(56) References Cited

U.S. PATENT DOCUMENTS

| | | | | |
|---|---|---|---|---|
| 2012/0046867 A1* | 2/2012 | Faber | ................... | G01N 23/222 |
| | | | | 702/8 |
| 2012/0109604 A1* | 5/2012 | Chen | ..................... | G01V 11/00 |
| | | | | 703/2 |
| 2013/0046469 A1* | 2/2013 | Herron | ............... | G01N 21/3563 |
| | | | | 702/2 |
| 2014/0032131 A1* | 1/2014 | Owen | ................ | G01N 23/2252 |
| | | | | 702/28 |
| 2015/0260034 A1* | 9/2015 | Herron | ................... | G01N 33/24 |
| | | | | 702/11 |
| 2016/0266275 A1* | 9/2016 | Akkurt | ................... | E21B 49/00 |

OTHER PUBLICATIONS

Herron et al., Application and Quality Control of Core Data for the Development and Validation of Elemental Spectroscopy Log Interpretation, SPWLA, vol. 55, Issue 05, Oct. 2014, 23 pages.

Herron et al., Dual-Range FT-IR Mineralogy and the Analysis of Sedimentary Formations, Proceedings Paper No. SCA-9729, Proceedings of the International Symposium of the Society of Core Analysts, 1997, 11 pages.

\* cited by examiner

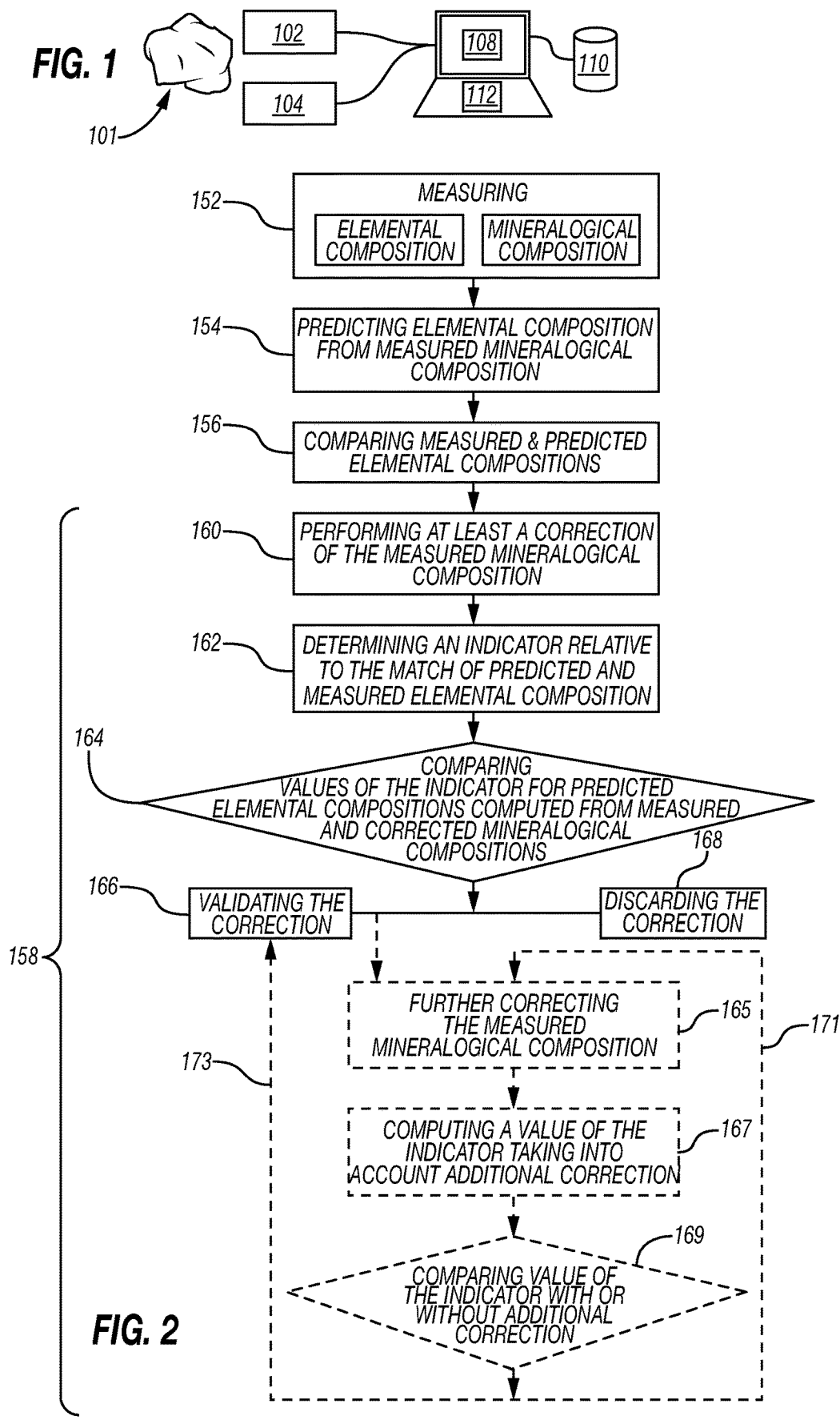

METHOD AND INSTALLATION FOR DETERMINING AN IMPROVED MINERALOGICAL COMPOSITION OF A ROCK SAMPLE

CROSS REFERENCE TO RELATED APPLICATIONS

This application claims priority to and the benefit of European Patent Application No. 17290103.5, titled "Method and Installation for determining an improved mineralogical composition of a rock sample," filed Aug. 16, 2017, the entire disclosure of which is hereby incorporated herein by reference.

BACKGROUND

The present disclosure relates to a method for determining a mineralogical composition of a sample of a geological formation.

When exploring a oil field, data concerning the oil field are gathered in order to determine the nature of the formation and to obtain indication of the presence of oil. In this context, it is common to collect samples from the formation such as drill cuttings and obtain the mineralogical composition of the sample (which constitutes critical information) via specific measurements. The measurement is preferably performed in the field to have the information available as soon as possible. To be able to estimate the mineralogical composition in the field, some techniques with simplified sample preparation such as DRIFTS (Diffuse Reflectance Infrared Fourier Transform Spectroscopy) or XRD (X-Ray Diffraction) have been developed.

Of course, it is sought to obtain a mineralogical composition as accurate as possible with the available measurement. To have an indication of the quality of measurement, Schlumberger has already developed a quality control procedure called QCMIN, disclosed for instance in the paper "*Application and Quality Control of Core Data for the Development and Validation of Elemental Spectroscopy Log Interpretation*" (Herron, Herron, Pirie, Saldungaray, Craddock, Charsky, Shray, Li, SPWLA, 2014), based on the cross-checking of the mineralogical composition and the elemental composition of the sample, measured separately. The elemental composition may indeed be measured accurately via known technique.

SUMMARY

The disclosure relates to a method for determining a mineralogical composition of a sample of a geological formation, comprising collecting a rock sample, and estimating a mineralogical composition and an elemental composition of the sample based respectively on first and second measurements. Then, the method includes, based on a mineralogy break-down model, estimating an initial predicted elemental composition of the sample from the mineralogical composition, and correcting the measured mineralogical composition of the sample based on the model to obtain a corrected mineralogical composition and a corresponding corrected predicted elemental composition. The correction may comprise adjusting an amount of at least a mineral within a family of minerals while the total amount of the minerals of the family is kept constant; correcting a total amount of a family of minerals within a system comprising a plurality of families of minerals while the relative amounts of each of the mineral within the family is kept constant; or adding an amount of an additional mineral distinct from the predetermined minerals while the relative amount of each of the predetermined minerals within the set of predetermined minerals, is kept constant, The method then comprises determining an indicator relative to the match of the predicted elemental composition and the measured elemental composition, and comparing the value of the indicator for the initial predicted elemental composition with the value of the indicator for the corrected predicted elemental composition, and outputting the measured mineralogical composition or the corrected mineralogical composition in view of the comparison result.

The elemental composition is indicative of relative amounts of predetermined chemical elements in the sample while the mineralogical composition is indicative of relative amounts of a set of predetermined minerals in the sample.

The disclosure relates to an installation for determining a mineralogical composition of a sample of a geological formation, comprising first and second detectors for measuring respectively a first and second characteristic of a rock sample, and a set of processing devices configured to estimate a measured mineralogical composition of the sample from the first characteristic and a measured elemental composition of the sample from the second, obtain an initial predicted elemental composition of the sample from the mineralogical composition, based on a mineralogy break-down model, and correct the measured mineralogical composition of the sample based on the model. The correction comprises adjusting an amount of at least a mineral within a family of minerals while the total amount of the minerals of the family is kept constant, correcting a total amount of at least a family of minerals within a system comprising at least two families of minerals while the relative amounts of each of the mineral within the family is kept constant, or adding an amount of an additional mineral distinct from the predetermined minerals while the relative amount of each of the predetermined minerals within the set of predetermined minerals, is kept constant. The set of processors is also configured for determining an indicator relative to the match of the predicted elemental composition and the measured elemental composition, comparing the values of the indicator for the initial predicted elemental composition and for the corrected predicted elemental composition, and outputting the measured mineralogical composition or the corrected mineralogical composition in view of the comparison result.

The installation and in particular the set of processors may be configured to implement all of the embodiments of the method described hereinafter.

The disclosure also related to a tangible computer readable medium comprising instructions for executing all of the embodiments of the method from the measurements received by the detectors.

The method and installation according to the disclosure improves the accuracy of the mineralogical composition based on known measurements, in particular for measurements performed in the field in near real-time.

BRIEF DESCRIPTION OF THE DRAWINGS

Various aspects of this disclosure may be better understood upon reading the following detailed description and upon reference to the drawings in which:

FIG. 1 is a schematic drawing of an installation according to an embodiment of the disclosure FIG. 2 is a flow diagram of a method according to an embodiment of the disclosure

DETAILED DESCRIPTION

Figure 3A:
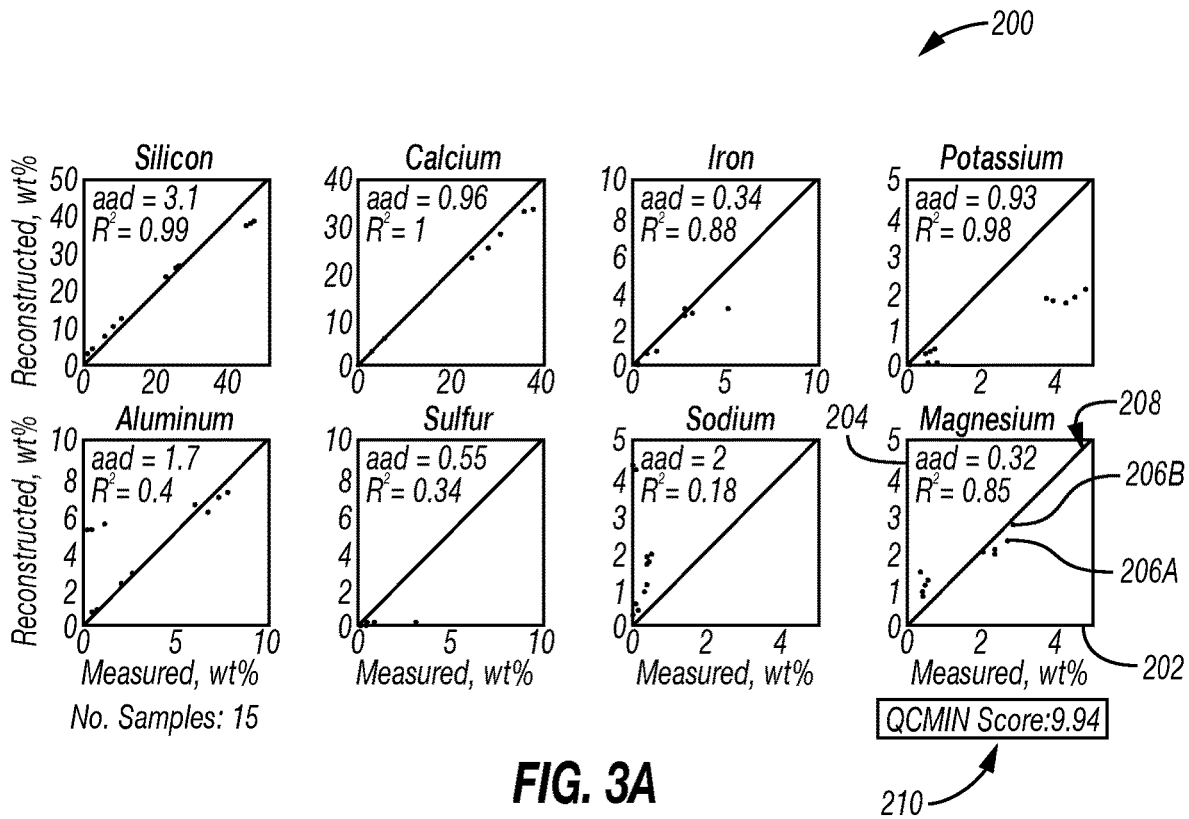
FIGS. 3A & 3B show plots representative of a quality control of a mineralogical composition estimated via a DRIFTS apparatus and determined as per the prior art (FIG. 3A) or as per the method of FIGS. 4 and 5 (FIG. 3B)

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.'

FIG. 1 discloses an installation for determining a mineral composition of a sample according to an embodiment of the disclosure. The installation may in particular analyze rock sample that are core samples obtained downhole from the formation or cuttings that have been collected at the surface during the drilling of a wellbore (for instance at the exit of the borehole at the shale shaker). The installation may be installed at the rig site, or remotely from the rig site or partially at the rig site and partially remotely.

The installation of FIG. 1 includes a first measurement device 102 for measuring a characteristic of a rock sample 101 that enables to derive a mineralogical composition of the sample and a second measurement device 104 for measuring an elemental composition of the rock sample 101. In the following, the terms "estimating the mineralogical composition" or "measuring the mineralogical composition" may be used but the reader should understand that the measurement of the first measurement device 102 does not give a direct measurement of the mineralogical composition.

The first measurement device may for instance be a DRIFTS (Diffuse Reflectance Infrared Fourier Transform Spectroscopy) apparatus, or a XRD (X-Ray Diffraction) apparatus but any other device suitable for measuring a characteristic enabling the estimation of the mineralogical composition may be used, such as infrared spectroscopy, ATR (Attenuated Total Reflection) spectrometry, Raman spectroscopy. All of these techniques are well-known in the art and not described in details therein. The first measurement device 102 measures a characteristic of the rock introduced in the first device (for instance a diffuse reflection produced by the sample in response to an infrared light in the case of DRIFTS) and obtains, in view of a calibrated model, a mineralogical composition of the sample, i.e. the amount in weight of every mineral in the sample. Minerals may be quartz, feldspar, chlorite, calcite, dolomite, etc. The mineralogical composition obtained directly from the first measurement device may depend on the nature of the apparatus that is used. For instance, a XRD apparatus does not output exactly the same minerals as the DRIFTS.

The second measurement device 104 may for instance be a XRF (X-Ray fluorescence) apparatus but any other device for measuring the elemental composition may be used, such as ICP-MS (Inductively Coupled Plasma Mass Spectrometry) apparatus or LIBS (Laser Induced Breakdown Spectroscopy). Such techniques are well-known in the art and not described in further details therein. The second measurement device 104 measures a characteristic of the rock introduced in the second device (for instance a fluorescence produced by the sample in response to a X-Ray light in the case of XRF) and obtains, in view of a calibrated model, an elemental composition of the sample, ie the amount in weight of every chemical element in the sample. Chemical elements may be aluminum, carbon, potassium, sodium, silicate, etc.

The installation according to the disclosure also includes a processing system 106, such as a computer but that may comprise several connected devices, including a processor 108 for executing programs comprising instructions and a memory 110 for storing the programs, data, or database. It may also include any appropriate user interface 112 (display, keyboard, etc.) The processing system may be connected to the first and second 102, 104 measurement device, for instance directly or via a local or global network and store the output from the devices in the memory. It may also store a program for obtaining a corrected, more accurate mineralogical composition of the sample in view of the measurements output from first and second devices 102, 104.

In a particular embodiment, all or part of the installation is situated at the rig site, for instance in a mud logging cabin so that the drill cuttings collected at the exit of the borehole may be analyzed in near real-time, right after the collection. However, the installation may be also situated away from the rig site, for instance in an analysis lab.

An embodiment of a method for determining a mineralogical composition of a rock sample is now described with respect to FIG. 1. First, elemental composition and mineralogical composition of the sample are estimated based on measurements (block 152). The sample may for instance be split into two subsamples, each measured in one of the devices 102, 104, or may be introduced sequentially in the first and second devices 102, 104. All necessary preparation operations for ensuring the best measurement possible may be carried out before introducing the sample in the corresponding device (such as, for instance, crushing the sample before submitting it to a DRIFTS measurement). Any appropriate preparation method may be used for carrying out the method of the disclosure and such method will therefore not be detailed here.

Then, from the mineralogical composition estimated directly from the measurement, called "measured mineralogical composition" in the following, the processing device predicts an elemental composition based on a mineralogical break-down model (block 154). This mineralogical break-down model is a model determining the percentage of each chemical element in each type of rocks. Such a model is for instance disclosed in "*Dual-Range FT-IR Mineralogy and the Analysis of Sedimentary Formations*" (Herron, Matteson and Gustavson) and consists in considering, for instance, that the calcite formula being $CaCO_3$, the amount of calcite is linked to the amount of calcium. Therefore, the processing device stores in the memory 110 a measured elemental composition (obtained from the second measurement device 102) and a predicted elemental composition (obtained from the first measurement device and the mineralogical break-down model). The processing device also compares the measured and predicted elemental compositions (block 156) and may compute values of an indicator for evaluating the match between the mineralogy and elemental composition. Such indicator may for instance be the sum of the absolute errors of a set of chemical elements of the predicted elemental composition versus the measured elemental composition. Such approach has already been implemented by Schlumberger, under the name of the QCMIN method as explained in more details in the document cited in the background section. The indicator chosen in the QCMIN method is the sum of absolute errors of all of the measured chemical elements and is used to assess the quality of the measurement.

An output of this approach is represented on FIG. 3A showing plots 200 representing the quality of the reconstruction for each of the main elements generally found in rocks (i.e. the 8 following elements: silicon, calcium, iron, potassium, aluminum, sulfur, sodium, magnesium). Each of the plot depicts the measured amount in weight of each of these elements thanks to the second measurement device in abscissa 202 versus the predicted amount in weight of the corresponding element determined through the measurement of the mineralogical composition (obtained via the first measurement device) and the mineralogy break-down model, in ordinate 204. The points 206A, 206B in each plot are representative of the values of each of the parameter obtained for a particular sample. As can be seen, several samples have been evaluated via the operations 150-156. On each of the plot, a diagonal line 208 is represented which corresponds to the line on which the points 206A, 206B should be situated if values of the predicted and measured elemental composition were identical. Variables relative to the linear regression (absolute average deviation aad and variance $R^2$) are shown on each of the corresponding plots.

The indicator, (here QCMIN Score 210) that is considered is the sum of the absolute average deviations for each of the eight measured elements.

The method of this disclosure includes additional operations. In particular, it includes improving (block 158) the accuracy of the mineralogical composition estimated from the first measurement. This operation includes performing at least a correction (block 160) of the measured mineralogical composition of the sample to obtain a corrected mineralogical composition and a corresponding corrected predicted elemental composition. This correction operation may comprise adjusting an amount of at least a mineral within a family of minerals while the total amount of the minerals of the family is kept constant, correcting a total amount of at least a family of minerals within a system comprising at least two families of minerals while the relative amounts of each of the mineral within the family is kept constant, or adding an amount of at least an additional mineral distinct from the predetermined minerals while the relative amount of each of the predetermined minerals within the set of predetermined mineral, is kept constant.

Indeed, it is known that minerals are grouped in families. The families include minerals having composition that are not identical but similar (such as carbonates, quartz-feldspar or clays). Adjusting an amount of at least a mineral within a family of minerals while the total amount of the minerals of the family is kept constant therefore corrects only the amount of the minerals belonging to a particular family. On the contrary, correcting a total amount of at least a family of minerals within a system comprising at least two families of minerals while the relative amounts of each of the mineral within the family is kept constant corresponds in adjusting the amount of clays relative to carbonates (for instance) without modifying the distribution of minerals within each of the family. Some of the mineral are not detected (here designated as additional minerals) by some measurement techniques enabling to derive mineralogical composition but may still be present in the mineralogical composition. At least one additional mineral may be added to the minerals that are detected (here designated as predetermined minerals) in order to assess if the mineralogical composition with additional mineral matches the elemental composition better and therefore if the additional mineral is present.

The improvement operation may also include determining (block 162) an indicator relative to the match of the predicted elemental composition and the measured elemental composition. This indicator may be determined at any time, not only at this moment of the operation sequence, or even stored in the memory 110 before the method has started. It may also include comparing (block 164) the value of the indicator corresponding to the initial predicted elemental composition with the value of the indicator for the corrected predicted elemental composition. In view of the result of the comparison, ie if the indicator comparison shows that the error is inferior with the corrected mineralogical correction than with the measured mineralogical composition, the method includes validating the correction (block 166), ie outputting the corrected mineralogical composition. On the contrary, if the indicator comparison shows that the error is superior with the corrected mineralogical correction than with the measured mineralogical composition, the method comprises discarding the correction, ie outputting the measured mineralogical composition (block 168). Alternatively, if the correction is assessed as efficient, the method may include further correcting the amount of a previously corrected mineral by adding or removing an additional predetermined amount to that mineral (block 165), computing a value of the indicator taking into account the additional correction (block 167) and comparing it with the previously computed indicator (block 169). This may be iteratively repeated (arrow 171) until the comparison indicates that the additional iteration of the correction does not provide a better match with elemental composition than the previous one (ie that the minimum of the error score has been reached after the previous iteration). In the latter case, the correction is validated (arrow 173) wherein the validated correction is the previously corrected mineralogy (and not the last one). Optionally, the corrections may also be validated even when the additional correction is more efficient than the previous correction but when a predetermined limit concerning the added or removed amount of minerals has been reached.

Figure 4:
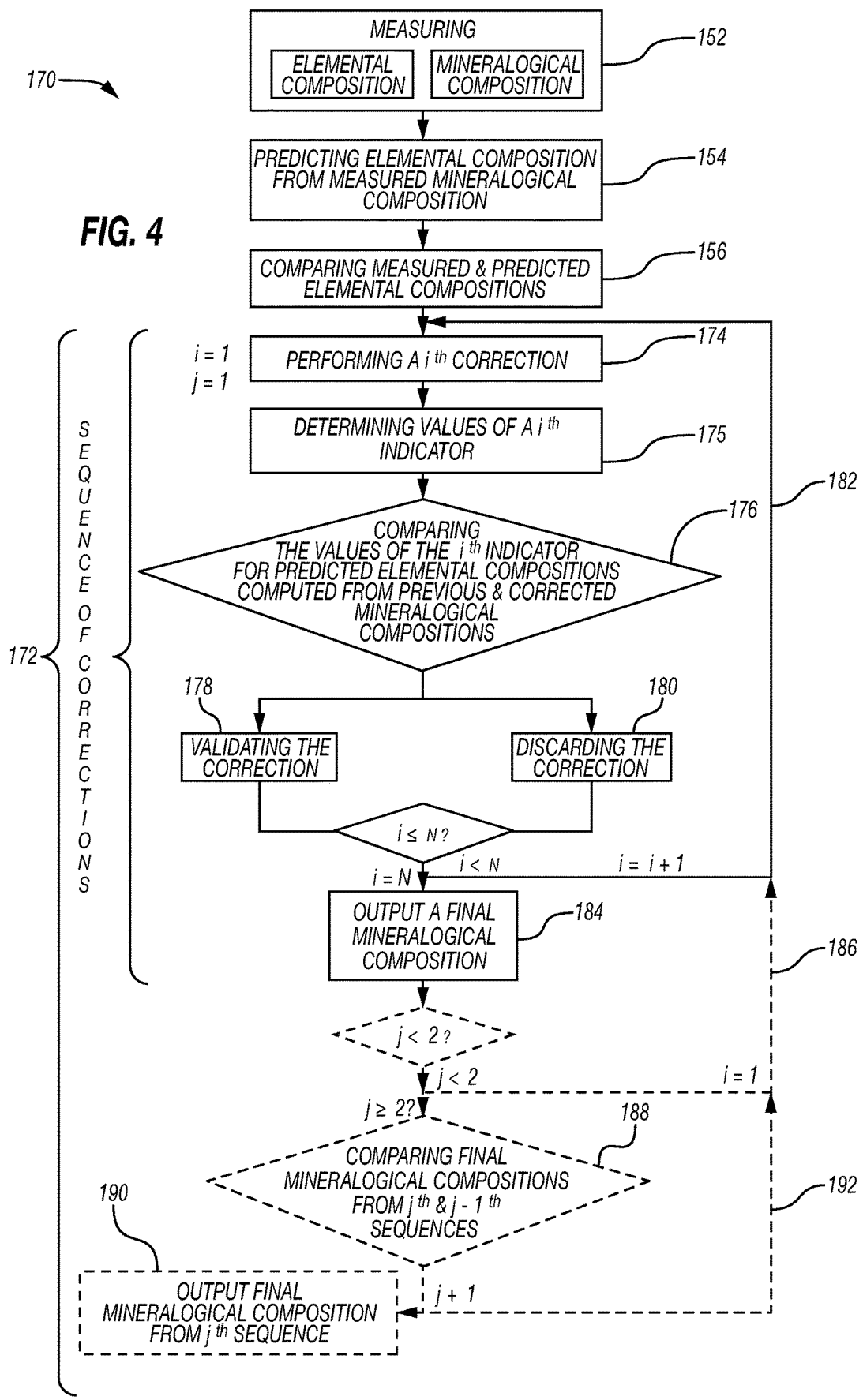
FIG. 4 is a flow diagram of the method according to another embodiment of the disclosure

Another embodiment of the method is disclosed in relationship with FIG. 4. The method 170 of FIG. 4 comprises, as for method 150, estimating the mineralogical composition and the elemental composition based on measurements (blocks 152) and predicting an elemental composition from the measured mineralogical composition (block 154) as well as comparing a measured and predicted elemental composition (block 156) as mentioned hereinabove. The measured composition is stored in the memory of the processor.

The method may then comprise improve the mineralogical composition (block 172). In this embodiment, the operation 172 includes a sequence of corrections performed iteratively. For instance, the sequence includes N corrections of different types. Each of this correction may include adjusting an amount of at least a mineral within a family of minerals while the total amount of the minerals of the family is kept constant, correcting a total amount of at least a family of minerals within a system comprising at least two families of minerals while the relative amounts of each of the mineral within the family is kept constant, or adding an amount of at least an additional mineral distinct from the predetermined minerals while the relative amount of each of the predetermined minerals within the set of predetermined minerals, is kept constant. Several corrections may be of the same type. For instance, one of the correction may include adjusting the amount of one or several minerals within a first family of minerals (for instance, carbonates), while another correction may include adjusting the amount of one or several within a second family (for instance, clays).

The operation 172 includes several corrections. It will be described in particular regarding a first correction. The operation includes performing a correction (block 174), such as a first correction. Performing the correction is as indicated above. It then comprises determining a value of an $i^{th}$ indicator associated to the $i^{th}$ correction (block 175), for each of the previous and $i^{th}$ corrected mineralogical composition. For instance, for the first correction, the previous mineralogical composition is the measured mineralogical composition and the indicator is a first indicator. The indicator may be an absolute error calculated on a first set of minerals, for instance when the correction is an adjustment within a family of minerals, on the set of minerals belonging to the family of minerals. The method then comprises comparing (block 176) the values of the indicator for the previous and corrected mineralogical composition, and in view of the result of the comparison, outputting and storing either the corrected mineralogical composition (block 178), ie validating the correction, or the previous mineralogical composition (block 180), ie discarding the correction. For the first correction, discarding the correction corresponds to outputting the measured mineralogical composition, if the comparison indicate that the correction does not improve the matching of the mineralogical and elemental compositions. Validating the correction corresponds to outputting the corrected mineralogical composition if the indicators indicate that the correction improves the matching of the mineralogical and elemental compositions.

Then, the method launches the next correction of the sequence (arrow 182) which includes the same operations as associated to the first correction, except that the $i^{th}$ indicator associated with the $i^{th}$ correction may be different from the first indicator associated to the first correction. It is noted that two indicators associated to two corrections may be identical. The indicators associated to all of the corrections may also be identical. Generally, the indicator is in relationship with the elements contained in the corrected minerals, such as the sum of absolute errors of the elements contained in the corrected minerals. The $i^{th}$ correction is performed on the basis of the composition output at the end of the $(i-1)^{th}$ correction. The second correction is for instance performed on the basis of the composition output at the end of the first iteration.

When the sequence of N corrections have been performed, the method may output the mineralogical composition obtained at the end of the sequence in replacement of the measured mineralogical composition (block 184).

In another embodiment, the method may include at block 184 storing the output of first correction sequence and relaunch the sequence of the N corrections (arrow 186). It then includes comparing the mineralogical composition output from the $j^{th}$ sequence of corrections with the one output from the $j-1^{th}$ sequence of corrections (block 188), for instance first and second sequences. If the outputs from $j^{th}$ and $j-1^{th}$ sequences are essentially identical, the method outputs the mineralogical composition output from the $j^{th}$ sequence of corrections (block 190). If they are not, the method includes re-launching a sequence of N corrections (block 192) and reiterating the operation 188 with the outputs of second and third sequence. In other words, the sequence of N corrections is performed several times until convergence of the corrected composition.

One example of the sequence of N corrections will be described below. This example is of course one of many other examples and it has to be noted that, in other sequence that are still in the scope of the disclosure, some corrections disclosed below may not be performed, other corrections may be added, the order of the corrections may be modified. Similarly, some of the indicators described as corresponding to a particular correction may differ from the indicators disclosed below. The corrections may vary in particular in view of the type of measurements (in particular measurement serving as a basis for mineralogical composition estimation) that are performed (for instance, DRIFTS measurement or XRD measurement). However, even with a same measurement, the correction patterns may not be identical to what is disclosed below.

Figure 5:
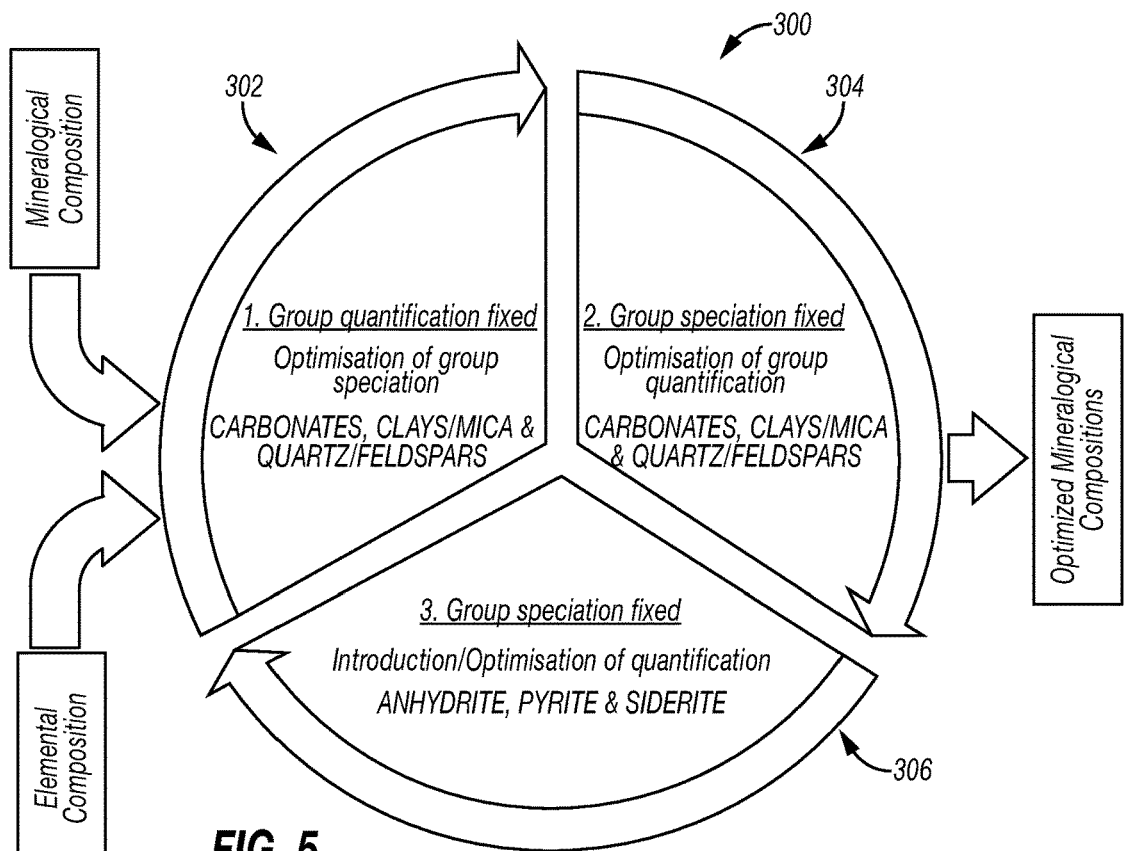
FIG. 5 is a flow diagram of a particular sequence of corrections that may be implemented in the method of FIG. 4

In this example, shown on FIG. 5, there are three types of corrections. In the embodiment, the corrections 300 comprises a first type of correction 302 consisting of adjusting an amount of at least a mineral within a family of minerals while the total amount of the minerals of the family is kept constant. The correction 302 is the first type of correction performed in the exemplary embodiment. It is performed for three types of families, namely the carbonates family, containing at least calcite and dolomite, the quartz and feldspar family, comprising at least quartz, Na-feldspar and K-feldspar, the Clays/Micas family comprising at least illite, chlorite, kaolinite and smectite.

For a particular family, indicators relative to specific minerals are monitored and the amount of the minerals is corrected to optimize the indicator. For instance, for the carbonates family, the indicator is the sum of absolute errors of the calcium and magnesium elements. When calcium is underestimated in the predicted elemental composition (based on the measured elemental composition), the correction consists in adding a predetermined amount of calcite and removing the predetermined amount of dolomite (so that the total amount of carbonates remains constant). If the indicator is optimized (ie the error score diminishes), a new addition of predetermined amount of calcite occurs, and so on. Of course, the condition is reversible, ie when the calcium is overestimated, the correction consists in removing the predetermined amount of calcite and adding the predetermined amount of dolomite.

For the quartz/feldspar family, the indicator is defined as the sum of absolute errors of the silicate, aluminum, potassium and sodium elements. In this case, as there are more than two minerals (quartz, Na-feldspar & K-feldspar), it is not as straightforward as for the carbonates family and several combinations of amounts are tested to optimize the indicator, ie diminishing the error score, while the total amount of minerals within the Quartz/Feldspar family is kept constant. Once again, this is an iterative process.

For the clays/mica family, the indicator is defined as the sum of all the eight measured elements that are shown on FIG. 3A. All the combinations of amounts may also be tested or the correction may be pre-constrained. For instance, when aluminum is underestimated in the predicted elemental composition and silicate overestimated, the correction consists in adding a predetermined amount of kaolinite and removing the predetermined amount of smectite (so that the total amount of carbonates remains constant). Of course, the conditions mentioned above are reversible. As for the other families, the addition of the predetermined amount may be performed iteratively until the indicator value is optimized.

The second type of correction 304 is performed after the first type of correction 302 has been implemented for all of the identified families. It comprises correcting a total amount of at least a family of minerals within a system comprising at least two families of minerals while the relative amounts of each of the minerals within the family is kept constant. In other words, the mineral distribution within one family remains the same even if the total amount of the family is modified. The corrections 304 in the embodiment comprise three corrections, ie one for each of the combination of two families, namely carbonates & quartz/feldspar, carbonates & clays/mica, quartz/feldspar & clays/mica. Each correction consists in testing a large range of mixtures regarding the amounts of the two families and to select the amounts for which the associated selected indicator is optimized. The range of tested mixtures may be pre-constrained in view of the measured mineralogical composition. For instance, the tested range of amounts may be +/−10% relative to the measured value. Therefore, for instance, if Carbonates is 60% and Quartz-Feldspar 40% of the total amount of both families, the tested range of amounts may be for instance +/−10%; ie [50; 70] for the Carbonates and [30, 50] for the Quartz-Feldspar.

The indicator associated with each of the corrections may be the following:
  For the carbonates & quartz-feldspar correction, the sum of the absolute errors of the silicate, aluminum, potassium, sodium, calcium and magnesium elements,
  For the carbonates & clays/mica correction, the sum of the absolute errors of the silicate, aluminum, potassium, sodium, calcium, magnesium and iron elements,
  For the Quartz-Feldspar & Clays/Mica correction, the sum of the absolute errors of the silicate, aluminum, potassium, sodium, calcium, magnesium and iron elements.

When the second type of correction 304 has been performed, a third type of correction 306 is implemented, consisting in adding an amount of at least an additional mineral distinct from the predetermined minerals while the relative amount of each of the predetermined minerals within the set of predetermined minerals, is kept constant. Such additional mineral may for instance be anhydrite, pyrite or siderite. Depending on the first measurement device, some correction may become unnecessary or additional correction may be implemented.

The third type of correction consists in defining a matrix consisting of the predetermined elements and having a composition determined via the measurements and possibly also via the corrections previously implemented. The amount of the minerals in the matrix is not modified during the third type 306 of correction (contrary to first and second type 302, 304). However, an amount of a predetermined mineral may be added and the amount of matrix may be decreased so that it does not correspond to 100% of the final composition.

Concerning anhydrite, it may for instance be incriminated if sulfur and calcium are underestimated. Concerning pyrite, it may for instance be incriminated if both iron and sulfur are underestimated. Siderite may be incorporated if iron is underestimated. These conditions are reversible as well which means that, if there is a second iteration of the sequence of the N corrections, the first incriminated amount of the additional mineral may be decreased during the third type of correction. For instance if both sulfur and calcium are overestimated, the amount of anhydrite may be decreased.

The indicators for all of the corrections consisting in adding an amount of an additional mineral are the sum of absolute errors of all of the measured minerals.

Of course, this sequence of 9 corrections is an example. The sequence of correction may include only one correction or one type of the three types of correction disclosed above. The order may also be different from what has been disclosed above and all of the families may not be corrected depending of the measurement device, the location of the well, etc. Similarly, the additional minerals included are not always only and all of the three minerals that are disclosed hereinabove.

Figure 3B:
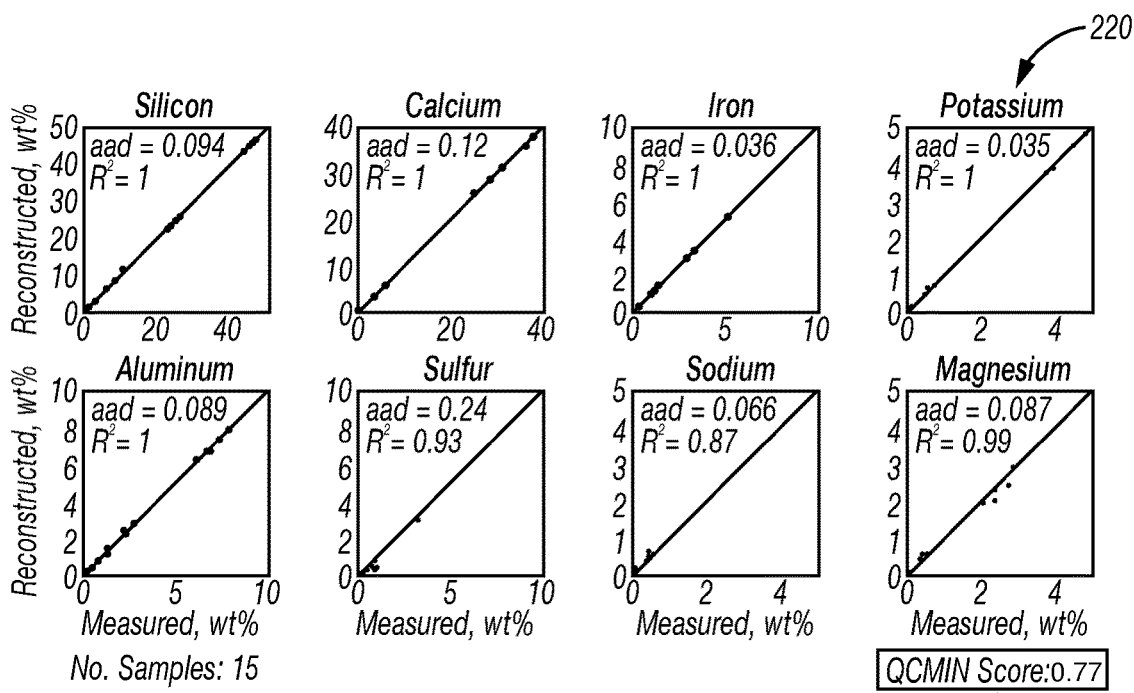

FIG. 3B shows the plots 220 representing the quality of the reconstructed mineralogical composition for each of the main elements generally found in rocks of FIG. 3A after implementation of the above-mentioned correction. It is clear that the average absolution deviation for each of the elements has significantly decreased and the QCMIN 230 score has been decreased by a factor greater than 10, which shows the benefit of the correction as it enables to determine a more accurate mineralogical composition, even including minerals that cannot all be measured by the mineralogical composition measurement device. It has to be noted that the mineral composition has been determined with a DRIFTS measurement apparatus for FIGS. 3A & 3B.

Figure 6A:
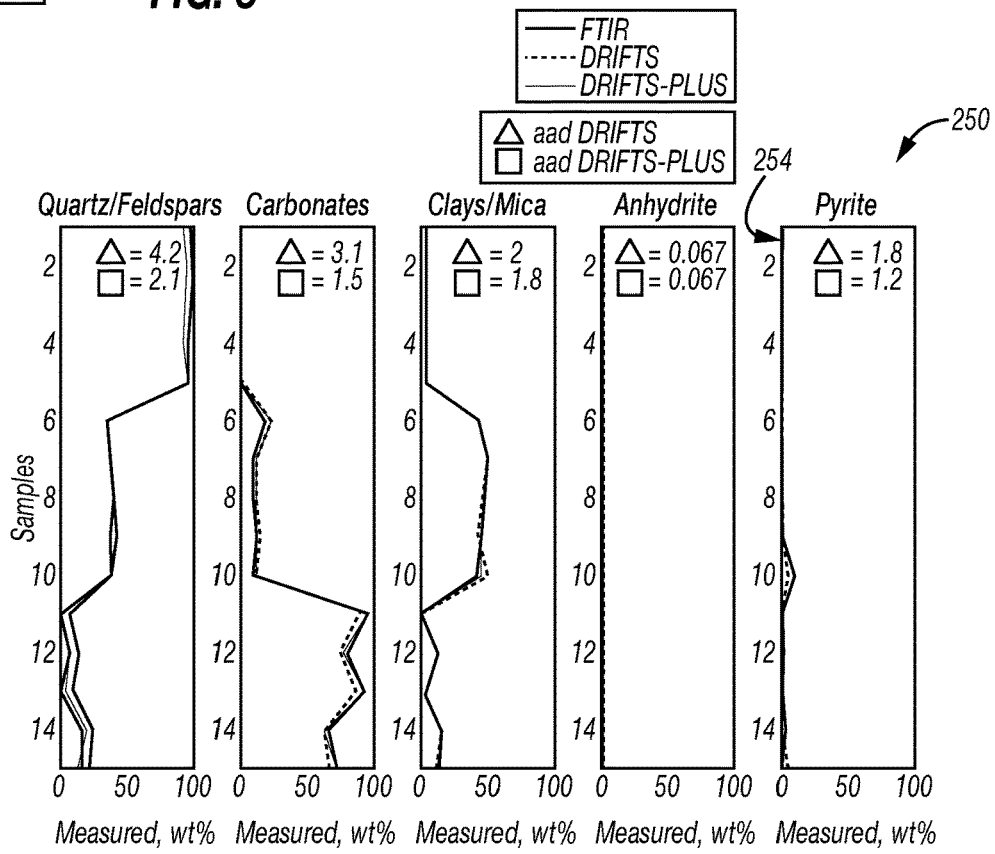
FIG. 6A-6D show plots of amounts of families of mineral (FIG. 6A) and minerals within each of the families (mica/clays on FIG. 6B, quartz-feldspar on FIG. 6C and carbonates on FIG. 6D) for different samples (also shown on plots of in FIGS. 3A & 3B), wherein the plots compare the amounts determines as per prior art and as per method of the disclosure to an amount estimated via a reference measurement.
Figure 6B:
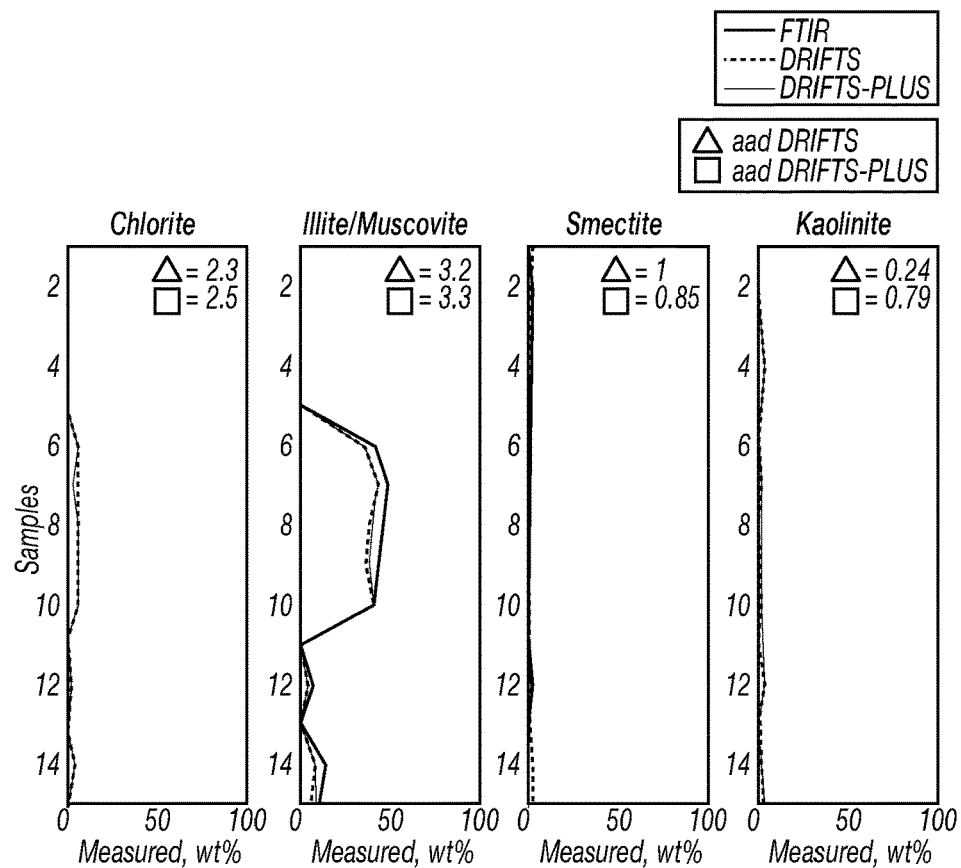
Figure 6C:
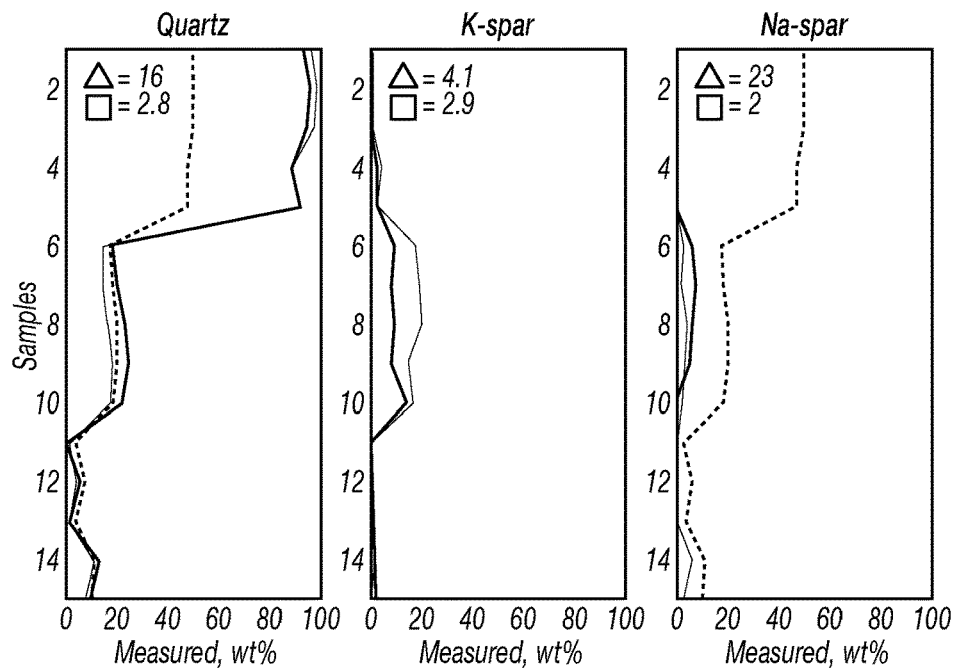
Figure 6D:
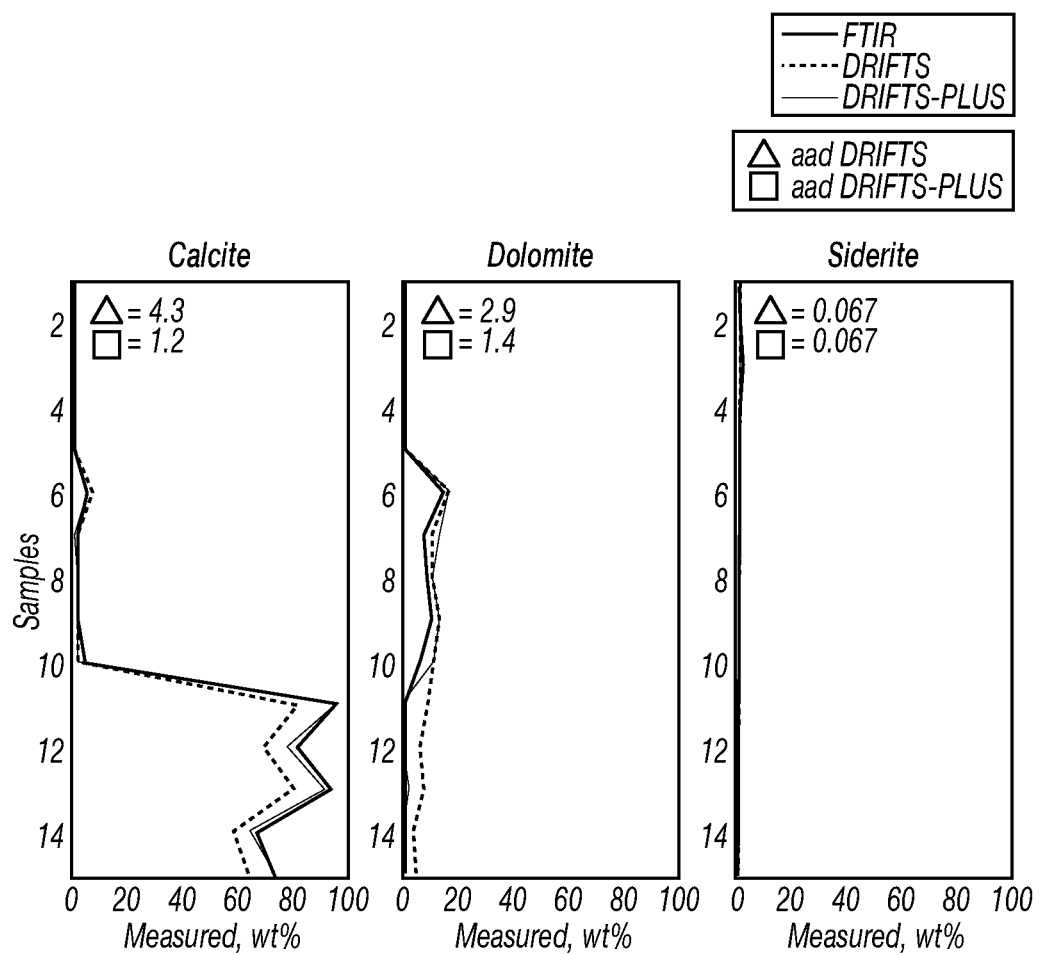

FIG. 6A-D also shows plots 250 of the measured amount in weight of each of the mineral families (FIG. 6A) or minerals of Clays/Mica family in FIG. 6B, Quartz-Feldspar family in FIG. 6C Carbonates family in FIG. 6D in each of the samples used for the correction of FIGS. 3A and 3B. Abscissa 252 shows the measured amount in weight (in %) while ordinate 254 is the number identifying each of the sample. The mineralogical composition has been measured in a laboratory with a reference instrumentation called FT-IR (see paper '*Dual-Range FT-IR Mineralogy and the Analysis of Sedimentary Formations*') (bold-lined curve) and is also represented as measured in the field with a DRIFTS apparatus, as per prior art ie without the correction (dotted-line curve) and as per the method according to the disclosure, ie with the correction (narrow-lined curve). The deviation of the DRIFTS measurement and correction DRIFTS measurement (called "DRIFTS-Plus") have been shown for each of the minerals. The correction clearly improves the match of the measured mineralogical composition with DRIFTS relative to the composition with the reference FTIR as the deviation of each of the curve either remains substantially the same or decreases, generally by a significant factor. This is particularly true regarding the Quartz-Feldspar family and the Carbonates family (though less significantly) while the Clays/Mica family amounts have not been modified significantly by the correction.

Figure 7A:
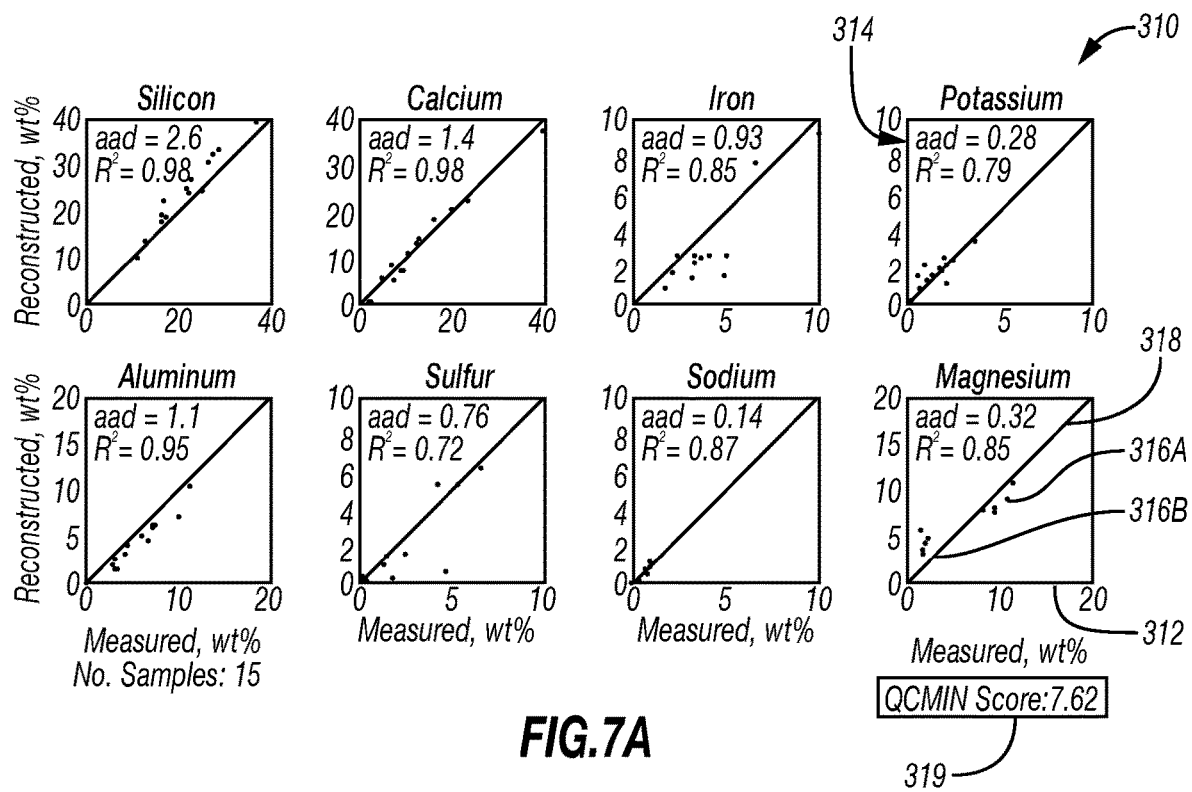
FIGS. 7A & 7B show plots representative of a quality control of a mineralogical composition estimated via a XRD measurement and determined as per the prior art (FIG. 7A) or as per the method of FIGS. 4 and 5 (FIG. 7B)
Figure 7B:
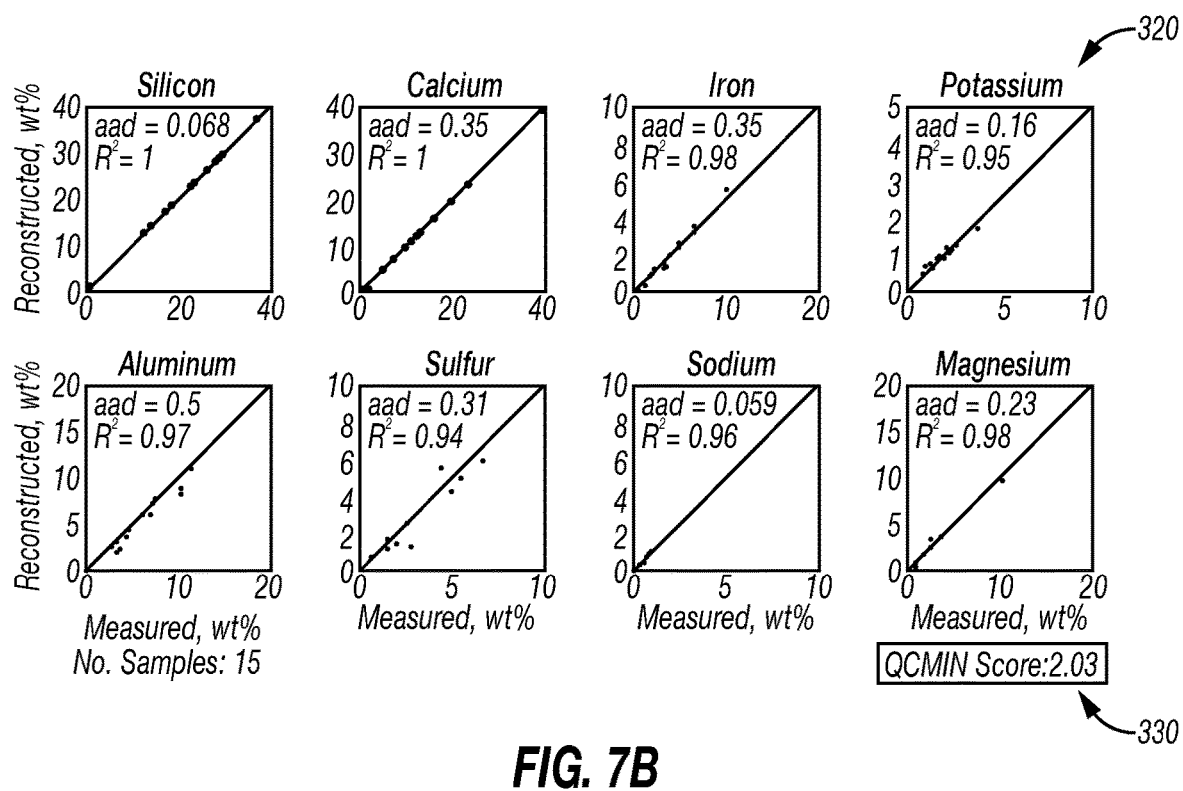

FIGS. 7A & 7B are equivalent to FIGS. 3A and 3B with the method of FIGS. 4 and 5 implemented on samples for which the measurement of the mineralogical composition has been measured with XRD. Similarly as FIG. 3A, plots 310 represent the quality of the reconstruction for each of the 8 main elements generally found in rocks. Each of the plot depicts the measured amount in weight of each of these elements thanks to the second measurement device in abscissa 312 versus the predicted amount in weight of the corresponding element determined through the measurement of the mineralogical composition (obtained via the first measurement device) and the mineralogy break-down model, in ordinate 314. The points 316A, 316B, in each plot are representative of the values of each of the parameter obtained for a particular sample. As can be seen, several samples have been evaluated via the operations 150-156. On each of the plot, a diagonal line 318 is represented which corresponds to the line on which the points 316A, 316B, should be situated. Variables relative to the linear regression (absolute average deviation aad and variance $R^2$) are shown on each of the corresponding plots. The indicator, (here QCMIN Score 319) that is considered is the sum of the absolute average deviations for each of the elements.

FIG. 7B shows the plots 320 representing the quality of the reconstruction for each of the main elements generally found in rocks of FIG. 7A after implementation of the correction of FIGS. 4 & 5. It is clear that the average absolution deviation for each of the elements has significantly decreased and the QCMIN score 330 has been decreased by a factor greater that 3. Therefore, the corrections as disclosed in reference with FIGS. 4 & 5 do not only apply to one specific measurement apparatus.

Figure 8A:
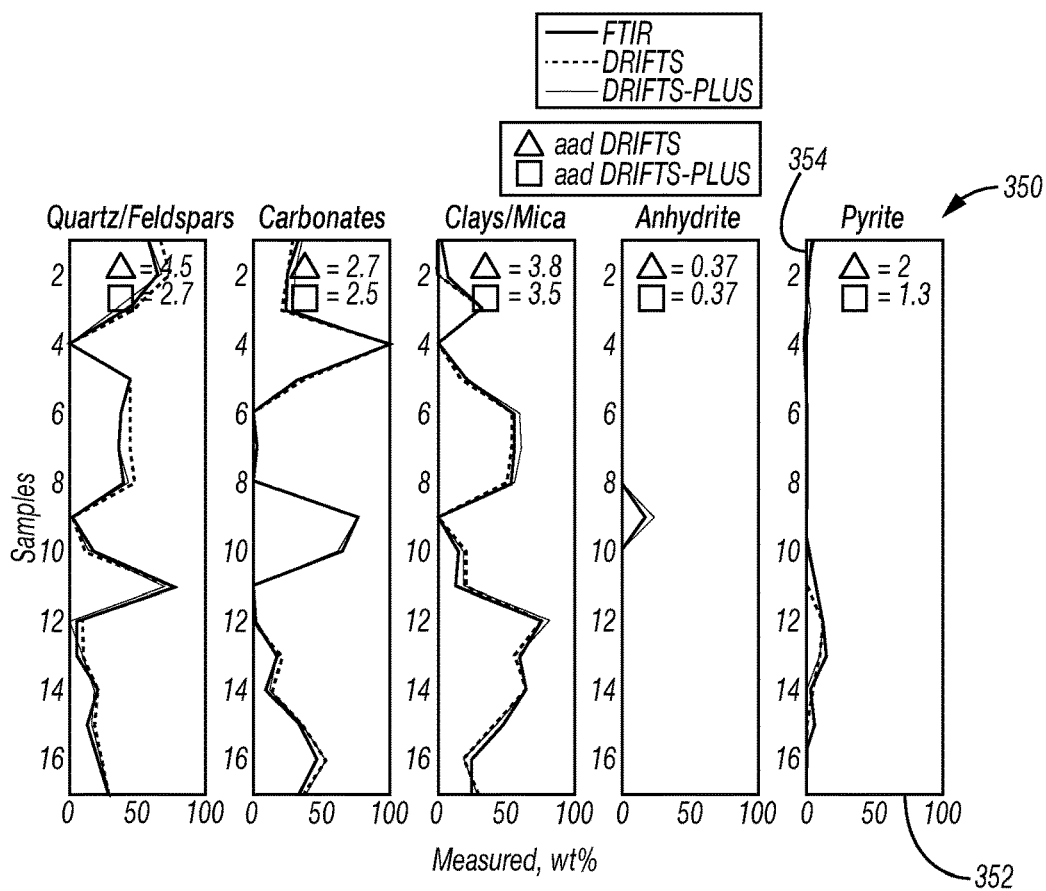
FIG. 8A-8D show plots of the amount of families of mineral (FIG. 8A) and minerals within each of the families (mica/clays on FIG. 8B, quartz-feldspar on FIG. 8C and carbonates on FIG. 8D) for different samples (also shown on plots of in FIGS. 7A & 7B), wherein the plots compare the amounts determines as per prior art and as per method of the disclosure to an amount estimated a reference measurement.
Figure 8B:
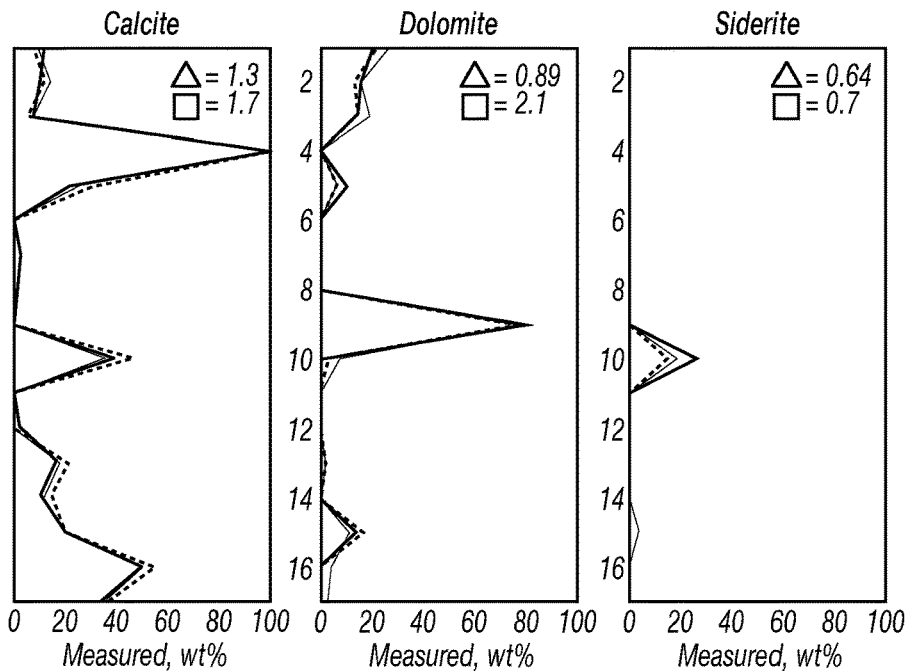
Figure 8C:
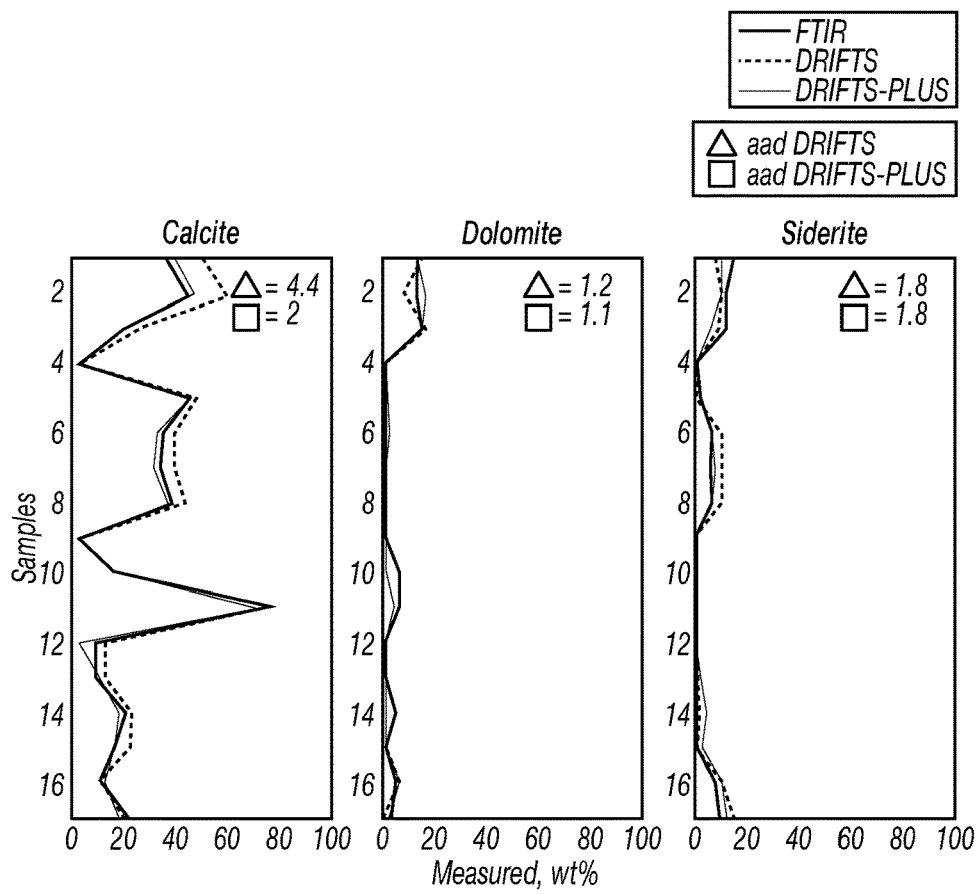
Figure 8D:
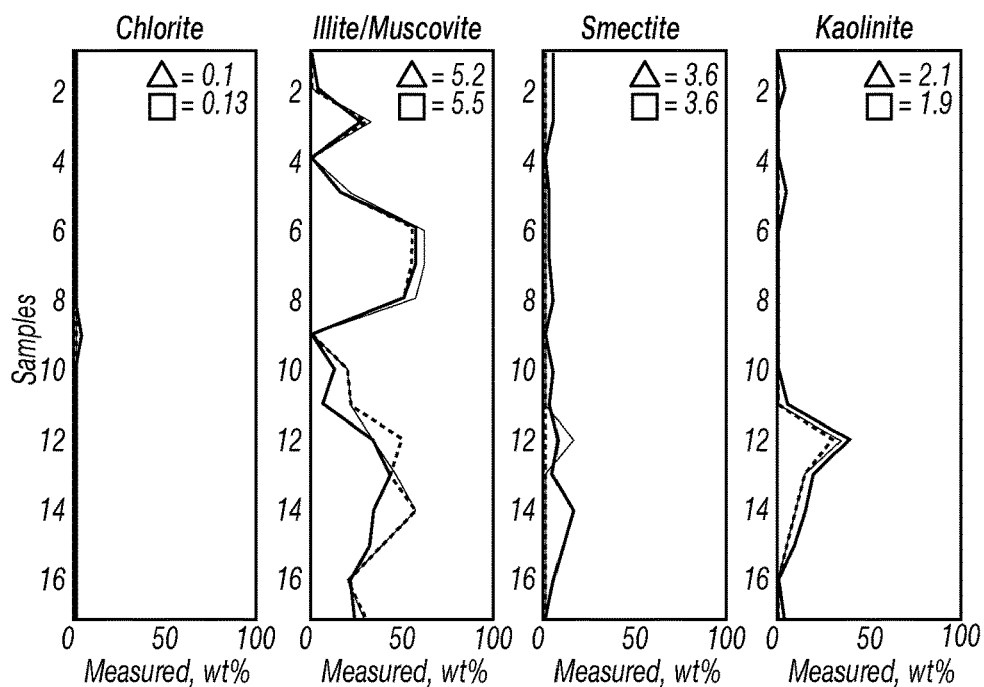

FIG. 8A-D also shows plots 350 of the measured amount in weight of each of the mineral families (FIG. 8A) or minerals of Carbonates family in FIG. 8B, Quartz-Feldspar family in FIG. 8C and Clays/Mica family in FIG. 8D in each of the samples used for the correction of FIGS. 7A and 7B. Abscissa 352 shows the measured amount in weight (in %) while ordinate 354 is the number of the sample. The mineralogical composition has been measured in a laboratory with a reference instrumentation called FTIR (bold-lined curve) and is also represented as measured in the field with a XRD apparatus, without the correction (dotted-line curve) and with the correction (narrow-lined curve). The deviation of the XRD measurement and corrected XRD measurement (called "XRD-Plus") have been shown for each of the minerals. It can be clearly seen that the correction improves the match of the measured mineralogical composition measured with XRD relative to the composition with the reference FTIR as the deviation of each of the curve either remains substantially the same or decreases, except for the dolomite. This is particularly true regarding the Quartz-Feldspar family.

While the invention has been disclosed with respect to a limited number of embodiments, those skilled in the art, having the benefit of this disclosure, will appreciate numerous modifications and variations there from. It is intended that the appended claims cover such modifications and variations as fall within the true spirit and scope of the invention.

The disclosure related generally to a method for determining a mineralogical composition of a sample of a geological formation, comprising collecting at least a rock sample originated from the formation, estimating a measured mineralogical composition of the sample based on a first measurement, estimating a measured elemental composition of the sample based on a second measurement, and based on a mineralogy break-down model, estimating an initial predicted elemental composition of the sample from the mineralogical composition. The method further comprises correcting the measured mineralogical composition of the sample to obtain a corrected mineralogical composition and a corresponding corrected predicted elemental composition based on the model, wherein the correction comprises at least one of the following:

adjusting an amount of at least a mineral within a family of minerals while the total amount of the minerals of the family is kept constant, correcting a total amount of at least a family of minerals within a system comprising at least two families of minerals while the relative amounts of each of the mineral within the family is kept constant adding an amount of at least an additional mineral distinct from the predetermined minerals while the relative amount of each of the predetermined minerals within the set of predetermined minerals, is kept constant, The method also comprises determining an indicator relative to the match of the predicted elemental composition and the measured elemental composition, and comparing the value of the indicator for the initial predicted elemental composition with the value of the indicator for the corrected predicted elemental composition, and outputting the measured mineralogical composition or the corrected mineralogical composition in view of the comparison result.

According to an embodiment of the disclosure, determining the indicator also comprises determining a difference between the relative amounts of a set of predetermined elements obtained from the predicted elemental composition and the relative amounts of the set obtained from the measured elemental composition. In this case, the correction may be validated if the difference is minimized for the corrected predicted elemental composition.

The method may include performing a correction sequence including:

performing a first correction of the measured mineralogical composition, determining a first indicator relative to the first correction, and based on the comparison of the values for the first indicator, outputting one of the initial and corrected mineralogical composition, performing a $i^{th}$ correction on the i–$1^{th}$ output mineralogical composition;

determining a $i^{th}$ indicator relative to the $i^{th}$ correction and based on the comparison of the values for the second indicator, outputting one of the i-1$^{th}$ output mineralogical composition and the i$^{th}$ corrected mineralogical composition wherein i≥2 and i∈N In this case, the indicator for each correction may be independent, identical to the other indicators or distinct from the other indicators. The correction sequence may also be performed iteratively until convergence or once.

A family of minerals may include one of the following:

Carbonates, containing at least calcite and dolomite

Quartz and Feldspar, comprising quartz, Na-Feldspar and K-Feldspar,

Clays comprising Illite and chlorite, kaolinite and smectite

The additional minerals may include pyrite or anhydrite or siderite.

The correction sequence may include adjusting the amount of at least a mineral within a family of minerals while the total amount of the minerals of the family is kept constant for each of the carbonates, quartz and feldspar and clays family.

The correction sequence may also or alternatively include correcting a total amount of at least a family of minerals within a system comprising at least two families of minerals while the relative amounts of each of the mineral within the family is kept constant, for each of the system of two families within the carbonates, quartz and feldspar and clays family, which might be performed once the adjustment of amount of minerals within the family has been performed for all the families.

Adding an amount of at least an additional mineral distinct from the predetermined minerals while the relative amount of each of the predetermined minerals within the set of predetermined minerals, is kept constant is performed for each of the pyrite, anhydrite and siderite, which may be performed once the correction of the total amount of at least a family of minerals within the system of two families has been performed for each of the system of two families within the carbonates, quartz and feldspar and clays family.

In an embodiment of the disclosure, a currently corrected amount of at least a mineral is iteratively corrected by adding or removing a predetermined amount to the previously corrected amount, wherein validating the correction includes selecting the previously corrected amount when the value of the indicator reached a local extremum for the previously corrected amount. In this case, validating the correction may comprise selecting the previously selected value when the currently corrected amount is not in a predetermined range.

The rock sample may be a drill cutting collected at a shale shaker of a surface installation of a rig. It may also be a core sample or any other type of rock sample.

The second measurement may be obtained with a XRF detector, while the first measurement is for instance obtained with a DRIFTS detector or a XRD detector The disclosure also generally relates to an installation for determining a mineralogical composition of a sample of a geological formation, comprising a first detector for measuring a first characteristic of a rock sample originated from the formation, and a second detector for measuring a second characteristic of the sample, as well as a set of processing devices comprising at least one processing device. The set of processors is configured to estimate a measured mineralogical composition of the sample from the first characteristic and a measured elemental composition of the sample from the second characteristic of the sample, obtain an initial predicted elemental composition of the sample from the mineralogical composition, based on a mineralogy breakdown model, and correct the measured mineralogical composition of the sample to obtain a corrected mineralogical composition and a corresponding corrected predicted elemental composition based on the model. The correction comprises at least one of the following:

adjusting an amount of at least a mineral within a family of minerals while the total amount of the minerals of the family is kept constant, correcting a total amount of at least a family of minerals within a system comprising at least two families of minerals while the relative amounts of each of the mineral within the family is kept constant adding an amount of at least an additional mineral distinct from the predetermined minerals while the relative amount of each of the predetermined minerals within the set of predetermined minerals, is kept constant, The set of processors are also configured to determine an indicator relative to the match of the predicted elemental composition and the measured elemental composition, and comparing the values of the indicator for the initial predicted elemental composition and for the corrected predicted elemental composition, and output the measured mineralogical composition or the corrected mineralogical composition in view of the comparison result.

The invention claimed is:

1. A method for determining a mineralogical composition of geological formation sample, the method comprising:
   (a) acquiring a rock sample from a geological formation;
   (b) measuring a mineralogical composition of the sample using a first measurement, the mineralogical composition being indicative of relative amounts of a set of predetermined minerals in the sample;
   (c) measuring an elemental composition of the sample using a second measurement, the elemental composition being indicative of relative amounts of predetermined chemical elements in the sample;
   (d) processing said measured mineralogical composition to compute a predicted elemental composition of the sample, said processing based on known elemental compositions of each of the predetermined minerals;
   (e) comparing said measured elemental composition and the predicted elemental composition to determine a first error indicator;
   (f) correcting the measured mineralogical composition to obtain a corrected mineralogical composition of the sample and processing the corrected mineralogical composition to compute a corresponding corrected predicted elemental composition of the sample;
   (g) comparing said measured elemental composition and the corrected predicted elemental composition to determine a second error indicator;
   (h) comparing the first error indicator and the second error indicator; and
   (i) outputting the measured mineralogical composition when the second error indicator is greater than the first error indicator in (h) or the corrected mineralogical composition when the second error indicator is less than the first error indicator in (h).

2. The method according to claim 1, wherein the rock sample is a drill cutting collected at a shale shaker of a surface installation of a rig.

3. The method according to claim 1, wherein the second measurement comprises an X-Ray Diffraction Fluorescence (XRF) measurement.

4. The method according to claim 1, wherein the first measurement comprises a Diffuse Reflectance Infrared Fourier Transform Spectroscopy (DRIFTS) measurement or an X-Ray Diffraction (XRD) measurement.

5. The method of claim 1, wherein said correcting in (f) comprises at least one of the following: (i) adjusting an amount of at least one mineral within a family of minerals while a total amount of minerals in the family remains constant, (ii) correcting a total amount of at least a family of minerals within a system including at least two families of minerals while relative amounts of each individual mineral with the family remains constant, or (iii) adding an amount of at least one additional mineral distinct from the predetermined minerals while relative amounts of each of the predetermined minerals within the set remains constant.

6. The method according to claim 5, wherein the family of minerals is selected from at least one of the following three types of mineral families: a Carbonate family comprising calcite and/or dolomite, a Quartz and Feldspar family, comprising quartz, Na-Feldspar and/or K-Feldspar, or a Clay/Mica family comprising Illite, chlorite, kaolinite and/or smectite.

7. The method according to claim 6, wherein said correcting in (f) comprises said adjusting in (i) for each of the Carbonate family, the Quartz and Feldspar family, and/or the Clays/Micas family.

8. The method according to claim 6, wherein said correcting in (f) comprises said correcting in (ii) for each of said systems of two families selected from the Carbonate family, the Quartz and Feldspar family, and/or the Clay/Mica family.

9. The method according to claim 8, wherein said correcting in (f) comprises said correcting in (ii) after said adjusting in (i) has been performed for each of the families.

10. The method according to claim 9 wherein said correcting in (f) further comprises said adding in (iii) after said correcting in (ii), wherein said adding is performed for each of pyrite, anhydrite, and siderite.

11. The method according to claim 5, wherein the additional mineral comprises at least one of pyrite, anhydrite, or siderite.

12. The method of claim 1, wherein:
(f) further comprises iteratively correcting the measured mineralogical composition to obtain other corrected mineralogical compositions of the sample and processing the other corrected mineralogical compositions to compute corresponding other predicted elemental compositions of the sample;
(g) further comprises comparing the other predicted elemental compositions with said measured elemental composition to determine corresponding other error indicators;
(h) further comprises comparing the other error indicators; and
(i) further comprises outputting one of the other corrected mineralogical compositions which has an error indicator having a lowest value.

13. The method according to claim 12, wherein said iteratively correcting is performed until a convergence of said other corrected mineralogical compositions is achieved.

14. The method according to claim 12, wherein said iteratively correcting comprises adding or removing a predetermined amount of a mineral to a previously corrected amount of the mineral, and wherein the previously corrected amount is selected when a value of the error indicator reaches a local extremum for the previously corrected amount.

15. A method for determining a mineralogical composition of geological formation sample, the method comprising:

(a) acquiring a rock sample from a geological formation;
(b) measuring a mineralogical composition of the sample using a first measurement, the mineralogical composition being indicative of relative amounts of a set of predetermined minerals in the sample;
(c) measuring an elemental composition of the sample using a second measurement, the elemental composition being indicative of relative amounts of predetermined chemical elements in the sample;
(d) processing said measured mineralogical composition to compute a predicted elemental composition of the sample, said processing based on known elemental compositions of each of the predetermined minerals;
(e) iteratively correcting the measured mineralogical composition of the sample to obtain corrected mineralogical compositions and corrected predicted elemental compositions of the sample;
(f) comparing the corrected predicted elemental compositions of the sample and said measured elemental composition of the sample to compute corresponding error indicators; and
(g) evaluating the error indicators to select and output one of the corrected mineralogical compositions.

16. The method of claim 15, wherein:
said iteratively correcting in (e) comprises at least one of the following: (i) adjusting an amount of at least one mineral within a family of minerals while a total amount of minerals in the family remains constant, (ii) correcting a total amount of at least a family of minerals within a system including at least two families of minerals while relative amounts of each individual mineral with the family remains constant, or (iii) adding an amount of at least one additional mineral distinct from the predetermined minerals while relative amounts of each of the predetermined minerals within the set remains constant.

17. The method of claim 16, wherein said iteratively correcting in (e) comprises first said adjusting in (i), followed by said correcting in (ii), and then said adding in (iii).

18. The method of claim 17, wherein said families of minerals are selected from at least one of the following three types of mineral families: a Carbonate family comprising calcite and/or dolomite, a Quartz and Feldspar family comprising quartz, Na-Feldspar, and/or K-Feldspar, or a Clay/Mica family including Illite, chlorite, kaolinite, and/or smectite.

19. The method of claim 17, wherein said adding in (iii) is performed for each of pyrite, anhydrite, and siderite.

20. An installation for determining a mineralogical composition of a sample of a geological formation, the installation comprising:
a first detector configured to measure a first characteristic of a rock sample acquired from a geologic formation;
a second detector configured to measure a second characteristic of the rock sample;
a set of processing devices comprising at least one processing device configured to:
(i) estimate a mineralogical composition of the sample from the first characteristic, the mineralogical composition being indicative of relative amounts of a set of predetermined minerals in the sample;
(ii) estimate an elemental composition of the sample from the second characteristic, the elemental composition being indicative of relative amounts of predetermined chemical elements in the sample;
(iii) process said estimated mineralogical composition to compute a predicted elemental composition of the sample, said processing based on known elemental compositions of each of the predetermined minerals;

(iv) iteratively correct the estimated mineralogical composition of the sample to obtain corrected mineralogical compositions and corrected predicted elemental compositions of the sample;

(f) compare the corrected predicted elemental compositions of the sample and said estimated elemental composition of the sample to compute corresponding error indicators; and (g) evaluate the error indicators to select and output one of the corrected mineralogical compositions.

\* \* \* \* \*